United States Patent
Godard

(10) Patent No.: US 10,451,770 B2
(45) Date of Patent: Oct. 22, 2019

(54) METHOD AND SYSTEM FOR MEASURING/DETECTING ICE OR SNOW ATMOSPHERIC ACCRETION ON OVERHEAD POWER LINES

(71) Applicant: Ampacimon S.A., Grace-Hollogne (BE)

(72) Inventor: Bertrand Godard, Seraing (BE)

(73) Assignee: Ampacimon S.A., Grace-Hollogne (BE)

( * ) Notice: Subject to any disclaimer, the term of this patent is extended or adjusted under 35 U.S.C. 154(b) by 57 days.

(21) Appl. No.: 15/424,387

(22) Filed: Feb. 3, 2017

(65) Prior Publication Data
US 2017/0227677 A1   Aug. 10, 2017

(30) Foreign Application Priority Data

Feb. 4, 2016   (EP) ..................................... 16154274
May 27, 2016  (EP) ..................................... 16171627

(51) Int. Cl.
| | |
|---|---|
| *G01W 1/06* | (2006.01) |
| *G01N 3/28* | (2006.01) |
| *G01W 1/14* | (2006.01) |
| *G01L 5/10* | (2006.01) |
| *H02G 7/04* | (2006.01) |

(Continued)

(52) U.S. Cl.
CPC .............. *G01W 1/06* (2013.01); *G01L 5/102* (2013.01); *G01L 5/107* (2013.01); *G01L 5/108* (2013.01); *G01W 1/14* (2013.01); *H02G 1/02* (2013.01); *H02G 7/04* (2013.01); *G01N 3/28* (2013.01); *H02G 7/16* (2013.01)

(58) Field of Classification Search
None
See application file for complete search history.

(56) References Cited

U.S. PATENT DOCUMENTS

| | | |
|---|---|---|
| 5,029,101 A | 7/1991 | Fernandes |
| 5,235,861 A | 8/1993 | Seppa |

(Continued)

FOREIGN PATENT DOCUMENTS

WO   WO 2014/090416 A1   6/2014

OTHER PUBLICATIONS

Slegers, James; Transmission Line Loading: Sag Calculations and High-Temperature Conductor Technologies; Iowa State University; pp. 1-24.*

Wang, Shaohua; Jiang, Xingliang; Progress in research on ice accretions on overhead transmission lines and its influence on mechanical and insulating performance; Front. Electr. Electron. Eng. 2012, 7(3): 326-336.*

(Continued)

*Primary Examiner* — Gregory J Toatley, Jr.
*Assistant Examiner* — Terence E Stifter, Jr.
(74) *Attorney, Agent, or Firm* — Reinhart Boerner Van Deuren P.C.

(57) ABSTRACT

The present invention is related to a method for detecting and/or measuring atmospheric accretion on a suspended electrical cable span (2) of overhead power lines, said suspended electrical cable span (2) having a sag (D) and a local tension (H), and being submitted to wind pressure ($w_{wind}$), comprising the steps of independently:

measuring said sag (D), and optionally measuring the wind pressure ($w_{wind}$), over a first time range, measuring the local tension (H) over a second time range, the results of both steps being complemented and/or combined, so that to allow atmospheric accretion detection and/or measurement.

17 Claims, 6 Drawing Sheets

(51) Int. Cl.
*H02G 1/02* (2006.01)
*H02G 7/16* (2006.01)

(56) References Cited

U.S. PATENT DOCUMENTS

| | | | | |
|---|---|---|---|---|
| 5,341,088 | A * | 8/1994 | Davis | G01R 15/14 |
| | | | | 324/105 |
| 5,517,864 | A | 5/1996 | Seppa | |
| 6,343,515 | B1 | 2/2002 | Dodson | |
| 7,424,832 | B1 | 9/2008 | Nunnelee | |
| 8,002,592 | B2 * | 8/2011 | Crutcher | G01R 15/142 |
| | | | | 439/783 |
| 8,184,015 | B2 * | 5/2012 | Lilien | H02G 1/02 |
| | | | | 340/870.04 |
| 2007/0271081 | A1 | 11/2007 | Johnson et al. | |
| 2014/0064389 | A1 | 3/2014 | Van Fleet et al. | |
| 2014/0123750 | A1 * | 5/2014 | Liu | G01W 1/02 |
| | | | | 73/170.17 |
| 2014/0145858 | A1 * | 5/2014 | Miller | H04Q 9/00 |
| | | | | 340/870.07 |
| 2014/0163884 | A1 * | 6/2014 | Lilien | G01P 5/02 |
| | | | | 702/3 |
| 2014/0283625 | A1 * | 9/2014 | Gallegos | G01G 19/14 |
| | | | | 73/862.391 |

OTHER PUBLICATIONS

Min Zhang, Yimeng Xing, Zhiguo Zhang and Qiguan Chen, Design and Experiment of FBG-Based Icing Monitoring on Overhead Transmission Lines with an Improvement Trial for Windy Weather, Sensors 2014, 14, 23954-23969; doi:10.3390/s141223954.
F. Kiessling et al., Overhead Power Lines, Planning, Design, Construction, Springer, 2003; 394 pages.
Moser, M.J., George, B. ; Zangl, H. ; Brasseur, G., Icing detector for overhead power transmission lines, Instrumentation and Measurement Technology Conference, 2009. I2MTC '09. IEEE, pp. 1105-1109.
http://www.combitech.se/; 2016; cited in the present application as "References" at end of patent specification.
http://www.powerlimit.be/; 2016; cited in the present application as "References" at end of patent specification.
http://www.powerlimit.be/files/uploads/Hf32.pdf; 2016; cited in the present application as "References" at end of patent specification.
https://www.tensitron.com/; 2016; cited in the present application as "References" at end of patent specification.
http://www.briceaust.com.au/DillonQCTM; 2016; cited in the present application as "References" at end of patent specification.
http://www.cooperinstruments.com/best-sellers/wire-tension-meters/; 2016; cited in the present application as "References" at end of patent specification.
http://russianpatents.com/patent/220/2209513.html; 2016; cited in the present application as "References" at end of patent specification.

* cited by examiner

METHOD AND SYSTEM FOR MEASURING/DETECTING ICE OR SNOW ATMOSPHERIC ACCRETION ON OVERHEAD POWER LINES

CROSS-REFERENCE TO RELATED APPLICATIONS

This patent application claims the benefit of European Patent Application No. 16154274.1, filed Feb. 4, 2016 and European Patent Application No. 16171627.9, filed May 27, 2016, the entire teachings and disclosure of which are incorporated herein by reference thereto.

TECHNICAL FIELD

The present invention relates to power engineering and particularly to a method and system or device for measuring/detecting atmospheric accretion of all possible types (ice, snow, wet snow, frost, etc. and any of their mixtures as for example rime icing), designated shortly hereinafter by ice accretion and/or atmospheric icing, with respect to a suspended span of cable of an overhead electrical power line. It also relates to the implementation of this method through a computer program or a memory carrier containing a computer-readable instruction set.

A real-time direct local measure/detection of ice accretion can be useful in a number of applications, and in particular for monitoring the transmission and distribution network since the accretion of ice, snow, wet snow, frost, etc. and their mixtures can lead to potential clearance violation, damage and power outages due to important static and/or dynamic mechanical overloads.

Atmospheric icing is a complex meteorological phenomenon and different meteorological conditions lead to a large variety of snow/ice and their mixtures deposits. Ice loads can cause significant damage to electric power transmission networks, especially in combination with wind. Overhead lines can collapse due to the mass of ice deposits, but also additional loads in conductors and support structures induced by so-called galloping oscillation can cause significant damage to the structures. These transient dynamic forces can also cause the cables to swing toward each other and/or toward the towers. Clashing of conductors and flashovers are the most common problems of transmission lines galloping. Repeating power interruption caused by flashovers (as flashovers cause circuit breakers to open) obviously reduces the service quality and can damage the circuit breakers. And also the conductors can be damaged due to the clashing and flashovers. Ice shedding may have similar consequences than galloping. Sudden ice shedding generates strong cable motion and high/severe dynamic loads, which can cause severe damages to the transmission lines such as tower arm failure or even cascading failures of several towers. Moreover non-uniform ice accretion on a conductor in adjacent spans results in a longitudinal load at the supports. Such loading may be created either by a non-uniform ice accretion as a consequence of the line exposure or owing to ice shedding and can cause severe damage to the transmission line structures.

The method and system according to the present invention could also be used in other devices measuring sag and/or tension.

BACKGROUND

Currently, on-line monitoring is widely applied to monitor power lines. As explained in U.S. Pat. No. 8,184,015, continuous monitoring of electrical power lines, in particular high-voltage overhead lines, is essential to timely detect anomalous conditions which could lead to a power outage. Measurement of power line spans between successive supports to determine whether the sag (clearance resp.) is lower (higher resp.) than an acceptable maximum (minimum resp.) value is becoming a mandatory requirement in some countries. Given the importance of power line monitoring, several devices and methods have been proposed to date in order to measure the sag and/or some other relevant parameters, either directly or indirectly related to sag. A number of different methods which perform sag measurement are known in prior art. According to some examples, sag of power lines monitoring can be performed by using models, weather models, measuring using image-processing and detection of a target installed on the conductor, measuring using a conductor replica attached to the tower to catch an assimilated conductor temperature without Joule effect, measuring the surface temperature of the phase conductor, measuring conductor tension, measuring using global positioning systems (GPS), measuring the angle of the conductor at the pole or at a location along span, measuring vibrations of the conductor, etc.

Indirect weather-based and/or model-based methods allow to determine sag from measured and/or simulated weather from models and corresponding estimated conductor temperature and supposed sag conditions. One drawback of these methods is that sag conditions are time changing, uncertain and not well-known in practice. These methods are not always capable of providing a correct picture of the situation. If for instance a snow or ice load appears on a line span, the calculation from weather to sag will be erroneous. Moreover, icing on structures highly depends on the temperature of these structures. In case of power lines, joule effect heats the conductor while weather conditions (mainly wind speed) at conductor location cool the conductor and must be adequately estimated. Due to local topology, this task may be very difficult. As joule heating and weather conditions are sensed by the conductor that determines its thermal equilibrium/temperature, point measurements of weather and in particular wind variables even taken in close proximity of the line remain inaccurate. The above comments and limitations are also valid for monitoring using a conductor replica attached to the tower to catch an assimilated conductor temperature without Joule effect.

Methods measuring the surface temperature of the phase conductor and methods measuring the angle of the conductor at the pole or at a location along span suffer from the same drawbacks: relation from temperature to sag can be uncertain and/or erroneous in case of icing and/or variations due to icing must be identified in sag variations along time using for example a temperature estimation.

Methods measuring sag using image processing and detection of a target installed on the conductor is sensitive to reduction of visibility induced by meteorological conditions, and in particular in case of ice fog and freezing fog.

A method measuring sag using global positioning systems (GPS), as detailed in U.S. Patent Application No. 2014/0064389 A1 does not give any information about ice overload.

U.S. Pat. Nos. 5,235,861 and 5,517,864 detail a power line monitoring using tension sensor measurement located at the pole. A drawback of this method is that relation from tension to sag can be uncertain and/or erroneous in case of icing because of unknown apparent conductor weight and/or variations due to icing must be identified in sag variations along time using for example a temperature estimation. The use of this tension installed/developed primarily for real-time ampacity rating also serves for observations of ice on conductors. As detailed in literature [2], the ice accretion can be determined by plots of tension versus net radiation temperature.

U.S. Pat. No. 6,343,515 B1 details a method and apparatus to perform a measure of tension in any location along a wire. Other older patents as for example U.S. Pat. No. 7,424,832 B1, use the same philosophy to measure the tension in a wire. As detailed in the cited patent, a deflection of the cable applied through the sensor produces a tangential force proportional to mechanical tension in the wire/cable. The deformation produced by the force is measured by an integrated strain gauge sensor. This sensor (output from strain gauge) must be calibrated to specific wire size and type. Commercial sensors, of which not-limitative illustrations are given in ref. [5] to [8], based on the corresponding method and apparatus detailed in the cited patents, are also available but these sensors are not directly usable in the domain of power lines domain since no attention was paid therein to high voltage constraints, as for example need for electromagnetic shielding of the monitoring electronics, anti-corona design, etc. Regarding ice monitoring of power lines, this tension-based method suffers from previously mentioned drawbacks as the fact that relation from tension to sag can be uncertain and/or erroneous in case of icing because of unknown apparent conductor weight, and/or variations due to icing must be identified in sag (tension) variations along time using for example a temperature estimation.

In another example, sag of power lines monitoring can be performed by measuring vibrations of the conductor as detailed in U.S. Pat. No. 8,184,015. As detailed in the above-mentioned patent, sag is solely determined by the fundamental frequency estimation of the vibrations of the conductor.

Except for vibrations-based sag monitoring detailed is U.S. Pat. No. 8,184,015, for which no external data such as topological data, conductor (and in particular apparent weight per unit length as explained further) or span data, weather data, or sagging conditions, etc., are needed for sag monitoring, all other methods exhibit at least some limitations in sag monitoring in case of ice loading periods as ice/snow or other accretion that build up on the conductor will increase the apparent diameter and weight of the conductor. In other words, the relation from measured parameters to sag is not known in case of atmospheric accretion. As a consequence, the previous methods, except in case of the vibrations-based method, can lead to errors in sag measurement due to atmospheric accretion and these methods eventually must be coupled to weather measurements/information to give data about ice-snow accretion conditions and/or conductor temperature (as conductor temperature is around 0° C. in case of accretion) but there is no information about ice accretion. The needed weather conditions coming from models and/or weather stations may not be a good estimate of the real weather conditions at conductor location or height, and estimated conductor temperature along the line could be erroneous.

Previously, sag monitoring systems were directly related to dynamic line rating of power lines. Sag increase can be due to various factors, such as previously mentioned: change on current load, change on weather conditions, etc. In order to distinguish between cases of increased sag for the line caused on the one hand by snow/ice loads and on the other hand by high line temperature due to current load and/or weather change, sag increase measurement is in practice set in connection with a conductor temperature measurement and/or a conductor temperature estimation since snow and/or ice load can occur at temperature around 0° C. Some functions have been built in to set threshold values for line temperature beforehand.

However, methods and systems which are not directly linked to dynamic line rating of power lines, and intended for measuring/detecting the potential ice thickness exist.

As explained in ref. [1], traditional methods of estimating icing conditions include video surveillance, non-contact infrared measurement, and temperature sensing at the line surface or core. As explained in ref. [1] as well, Bragg grating (FBG) sensing has exhibited a great potential in transmission line monitoring. Ref. [1] shows that icing monitoring can be achieved using FBG sensors. A drawback of such methods however is that the camera must be power supplied close to the power line. This method is sensitive to reduction of the visibility induced by meteorological conditions while indirect temperature-based and FBG methods is only a part of the solution. Indirect measurements are inaccurate since sag has to be deduced by algorithms which depend on unavailable and/or uncertain data (e.g. ice, wind loading) and/or uncertain models. Sag cannot thus be accurately determined by temperature or indirect measurements in case of atmospheric icing.

As explained for instance in ref. [3] and [9], icing and the thickness of the ice layer on an overhead power line can be determined by measuring inter-electrode capacitance formed by two electrodes mounted on the surface of the conductor by exploiting the time signals and differences in the respective permittivities of air, ice and water. This is only a part of the monitoring of the power lines since sag cannot be determined.

Other methods can be found in prior art. For instance the ice load surveillance sensor IceMonitor™ (detailed in ref. [4]) measures ice growth deposit on structures. A drawback of this system is that the sensor is not taking into account the current in the power line and the real conductor temperature which can be dramatically different from that of the above-mentioned sensor. Indeed, icing appears at conductor temperature around 0° C. and a small amount of current can lead to conductor temperature above the threshold of icing. Sag is not monitored at all and this specific ice monitor is only a part of the solution.

Most of the proposed methods measure some related parameters, which are then used to indirectly compute the overhead conductor sag. Sag variations due to icing must be identified by using a coupled temperature estimation since sag variations can be due to icing and/or change in conductor temperature (at high current for example).

SUMMARY OF THE INVENTION

A first aim of this disclosure is to provide a method for measuring/detecting accretion of ice-snow and/or their mixtures on power lines by measuring/detecting a change in the apparent weight per unit length of a conductor with respect to a suspended cable span which is due to accretion and which has a value reflective of the additional load of ice-snow and/or their mixtures on the entire suspended cable span.

Accordingly, in at least one illustrative embodiment, this method comprises the step of monitoring the sag of said suspended cable span over a first time interval, and the step of monitoring the mechanical tension of said suspended cable span during a second time interval, the first and the second time interval being usually the same or slightly different.

By measuring time evolution of both above-mentioned respective sag and tension, it becomes possible to determine accretion of ice, snow or mixtures thereof for which a change in apparent weight of conductor is observed.

BRIEF DESCRIPTION OF THE DRAWINGS

The invention may be more completely understood in consideration of the following detailed description of embodiments in connection with the accompanying drawings, in which.

Figure 1:
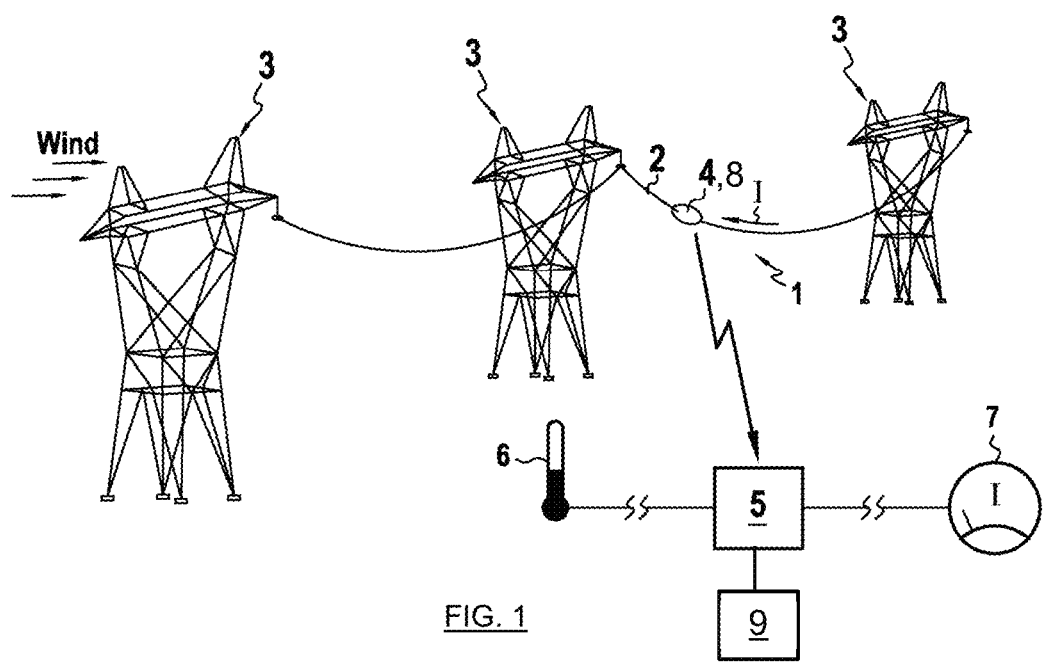
FIG. 1 is a schematic view of a power line with a plurality of spans of suspended electrically conductive cable and a system for measuring/detecting accretion of all possible atmospheric types (ice, snow, wet-snow, frost, etc. and mixtures thereof) with respect to a suspended span of cable.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the scope of the claims.

DETAILED DESCRIPTION

For the following defined terms, these definitions shall be applied, unless a different definition is given in the claims or elsewhere in this specification.

All numeric values are herein assumed to be preceded by the term "about", whether or not explicitly indicated. The term "about" generally refers to a range of numbers that one of skill in the art would consider equivalent to the recited value (i.e. having the same function or result). In many instances, the term "about" may be indicative as including numbers that are rounded to the nearest significant figure.

Any recitation of numerical ranges by endpoints includes all numbers within that range (e.g., 1 to 5 includes a.o. 1, 4/3, 1.5, 2, e, 2.75, 3, π, 3.80, 4, and 5).

Although some suitable dimension ranges and/or values pertaining to various components, features and/or specifications are disclosed, one of skill in the art, incited by the present disclosure, would understand that desired dimensions, ranges and/or values may deviate from those expressly disclosed.

As used in this specification and in the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

The present disclosure relates to measuring/detecting accretions of all possible types (ice, snow, wet-snow, frost, etc. and the mixtures thereof) with respect to a suspended span of cable or for an electric power line comprising such a suspended cable span.

It may nevertheless have other applications in fields not directly related to electric power transmission.

The present invention provides a new method and device for detecting/measuring atmospheric accretion on power lines by means of two independent measures/methods, the results of which being complemented and combined. These two methods determine the apparent weight of conductor and corresponding amount of ice/snow (and their mixtures) on power lines:

(i) the measurement of the sag in the suspended span and
(ii) the measurement of the (local) tension of suspended span.

For a multiple-span section, the sensor according to the present invention has to be repeated on all spans or at least on spans intended to be monitored along the section.

FIG. 1 schematically depicts an overhead power line comprising a plurality of successive suspended spans 2 of electrically conductive cable 1 supported by pylons 3 through suspension chains. On each suspended cable span 2 intended to be monitored along the section is clamped an autonomous device 4, as disclosed for instance in above-mentioned U.S. Pat. No. 8,184,015, comprising an accelerometer set suitable for monitoring motion in at least two axes perpendicularly to the cable and a transmitter for transmitting motion data obtained by this accelerometer set to a remote data processing unit 5. The autonomous device 4 may be inductively powered by the electric current I flowing through the power line cable 1. The illustrated system also comprises at least one ambient temperature sensor 6 and one electric current sensor 7 also connected to the remote data processing unit 5. The ambient temperature sensor 6 may be integrated within the autonomous device 4 or located within a general vicinity of the power line 1. The electric current sensor 7 may also be embedded within the autonomous device 4.

It has to be noted that it remains under the scope of the present invention to contemplate methods known in prior art for measuring the sag of the suspended span other than accelerometer methods, for example optical methods, in which a distance to an external target or to the ground is measured by a camera mounted on the suspended span or inclinometer methods measuring the angle made by the suspended span with the ground.

According to the present invention, an additional strain gauge 8 is further embedded in the autonomous device 4 for communicating local tension values 9 to the processing unit 5.

Figure 2:
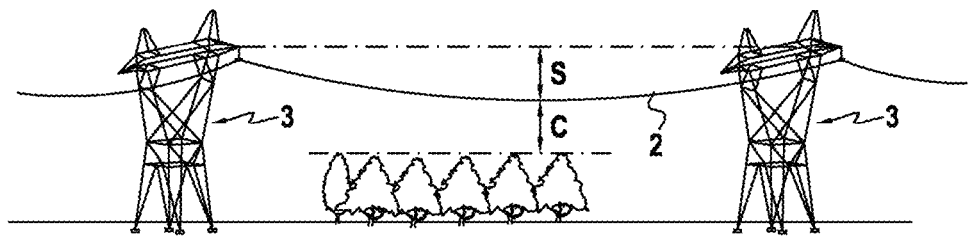
FIG. 2 is a side view of a span of the power line of FIG. 1

Each span 2 has a sag S which will increase with the temperature Tc of the cable, as thermal dilatation increases the length of cable between successive pylons 3. Increasing sag S of a suspended cable span generally decreases the clearance C of the cable with respect to the ground or any above ground obstacles, such as trees or buildings, as seen schematically on FIG. 2. It is however often required to maintain at least a critical minimum clearance C in order to prevent arcing from a suspended cable span of an overhead high-voltage power line.

Figure 3:
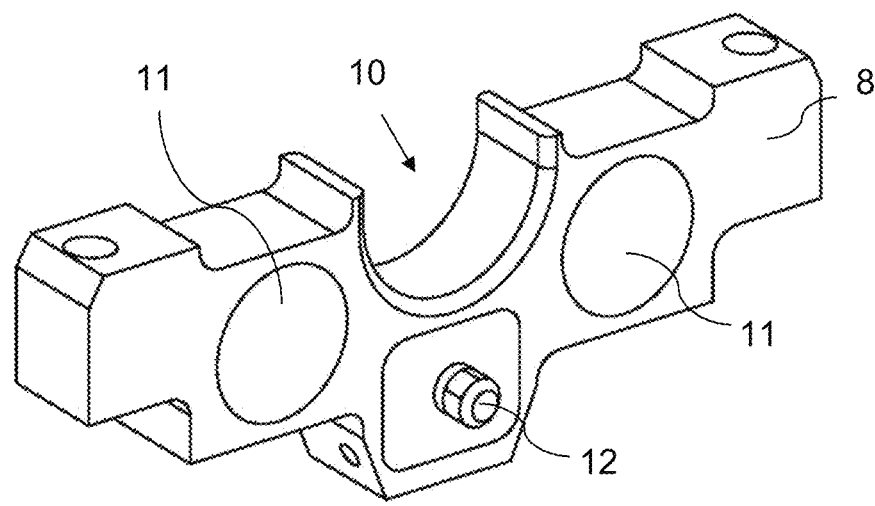
FIG. 3 is a perspective view of particular embodiment for a sensor according to the present invention.

FIG. 3 depicts an example of embodiment for the mechanical tension sensor 8 according to the present invention, comprising a cavity 10 for accommodating the electric cable and applying a deflection onto the cable. The cable deflection caused by the sensor device produces a tangential force which is proportional to the force exerted by the cable traction. On each side of this cavity 10 is a strain gauge 11 for measuring the tension caused by the deflection. Plug 12 is intended for connecting wires for power supply of the sensor as for recovering tension data.

Figure 4:
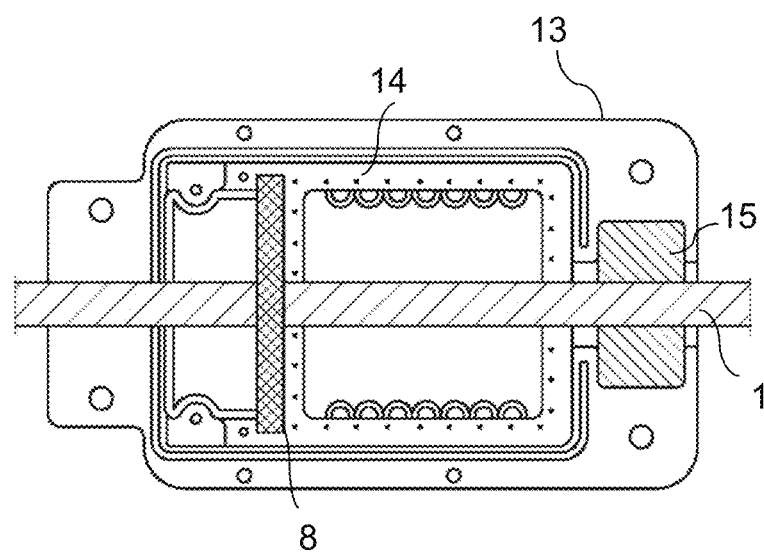
FIG. 4 is a cross-sectional view of a particular embodiment of the monitoring device according to the invention, taken along a horizontal (top) and vertical (bottom) plane, respectively. An imposed deflection through a tension sensor is schematically highlighted.
Figure 4:
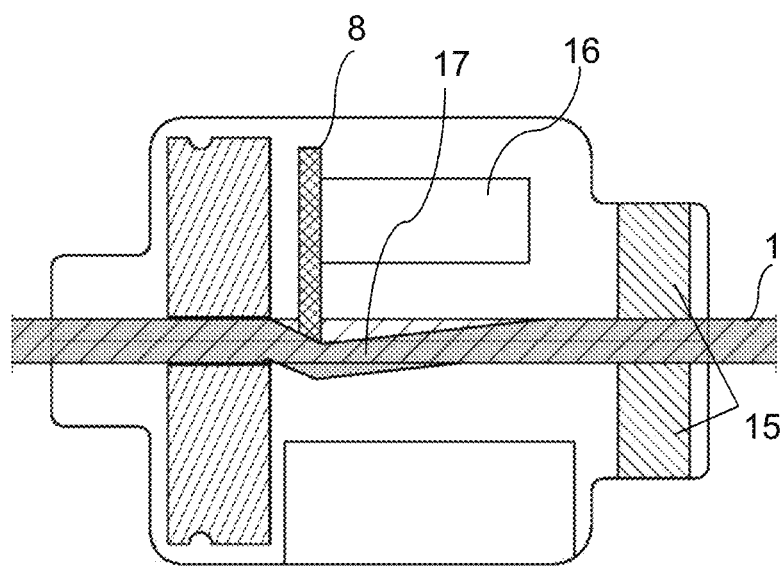

FIG. 4 schematically shows how tension sensor 8 is embedded in an accelerometer set casing as described for example in U.S. Pat. No. 8,184,015 B2.

In a purpose of analysis and explanation of the method, the computation and formulae are simplified by assuming a leveled span and uniform loading (i.e. conductor weight per unit length, ice and wind) along suspended cable. The sag of a suspended cable is well-known and well-defined in literature (see for example ref. [2]). It is given by the following parabola formula:

$$D = \frac{wL^2}{8H} \quad (1)$$

where D [m] is the sag, H [N] is the mechanical tension and L [m] is the span length, w [N/m] is the resultant force of conductor weight, wind pressure and ice loading, per unit length, given by $$w = \sqrt{(w_c + w_{ice})^2 + w_{wind}^2} \quad (2)$$

where $w_c$ [N/m] is the weight of conductor per unit length, $w_{wind}$ [N/m] is the pressure due to wind and $w_{ice}$ [N/m] is the potential additional weight due to any accretion (like ice loading); $w_{ice}$ and $w_c$ are acting in a vertical plane and $w_{wind}$ is acting on a horizontal plane. In case of no accretion and no wind, the resultant weight per unit length is equal to conductor weight per unit length; mathematically speaking, one has then $w = w_c$.

By measuring/determining both above-mentioned sag and tension, it becomes possible to determine the change in conductor apparent weight due to ice. Using equation (1) and equation (2), we see that the product of both above-mentioned sag D and tension H gives a coefficient p which is directly linked to the total resultant weight per unit length $$DH = p = \frac{wL^2}{8} = \quad (3)$$

$$\frac{L^2}{8}\sqrt{(w_c + w_{ice})^2 + w_{wind}^2} = \frac{w_c L^2}{8}\sqrt{\left(1 + \frac{w_{ice}}{w_c}\right)^2 + \left(\frac{w_{wind}}{w_c}\right)^2}$$

First consider the case with either no wind or negligible pressure due to wind for simplicity. Equation (3) becomes $$DH = \frac{wL^2}{8} = \frac{L^2}{8}\sqrt{(w_c + w_{ice})^2} = \frac{(w_c + w_{ice})L^2}{8} = \frac{w_c L^2}{8}\left(1 + \frac{w_{ice}}{w_c}\right) \quad (4)$$

Noting $$\frac{d}{dt}[1/s]$$

the time derivation of equation (4) and noting that conductor weight $w_c$ and span length L are constant over time, the rate of accretion is given by $$\frac{d}{dt}(DH) = \frac{L^2}{8}\frac{dw_{ice}}{dt} \quad (5)$$

Sag D and tension H can be obtained in different ways. Although wind and corresponding wind pressure can be estimated using vibrations-based method as detailed in patent application WO 2014/090416 A1, wind pressure $w_{wind}$ is generally negligible compared to conductor weight per unit length and potentially problematic ice overload.

Vibration-based measurement as detailed in U.S. Pat. No. 8,184,015 B2 is preferably used since sag is determined hereby without need of data and in particular of data such as extra weight due to ice or snow accretion.

According to an embodiment of the invention, a local tension measurement using an imposed deflection of the cable inside the sensor (FIG. 4) at sensor location is preferably used since there is no need to uncouple conductor from tower during installation as it is done using tension measurement at tower location. Local tension measurement from imposed deflection of wire/cable gives a relation from raw outputs from strain gauges to real tension in wire which must be calibrated to specific wire size and type before installation.

Local tension can be measured at a suitable high sampling frequency, a few tens of hertz, for example 25 [Hz], just like the accelerations, while sag determination needs a few minutes, depending on sampling frequency of accelerations and frequency resolution needed, due to frequency analysis of the accelerations measured at this high frequency sampling. Thus, in some embodiments, tension and sag may at times cover time periods slightly different.

Figure 5:
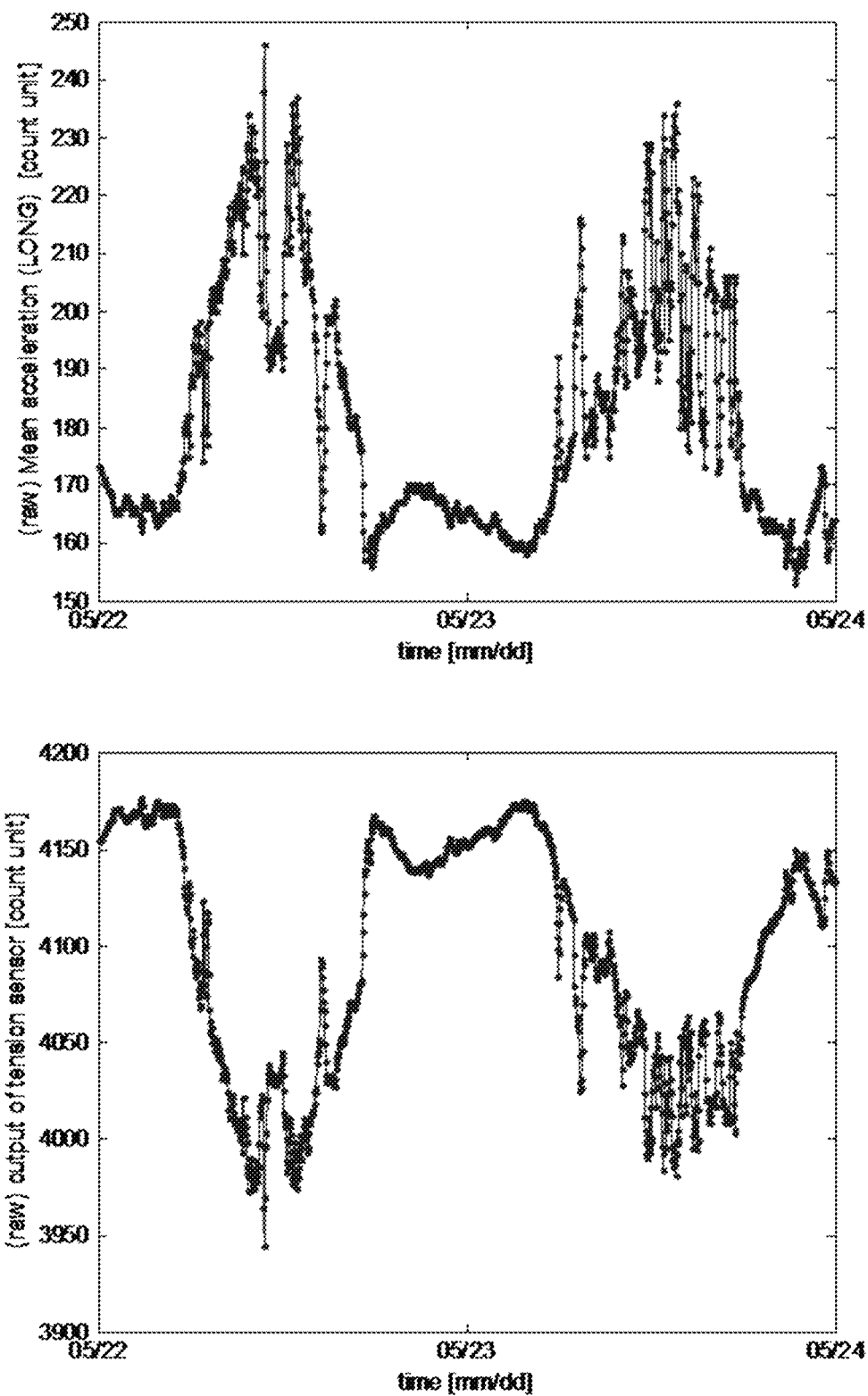
FIG. 5 is a graph showing, respectively, the evolution of sag (top) and tension (bottom) during a two-day period with no ice and negligible wind pressure.
Figure 6:
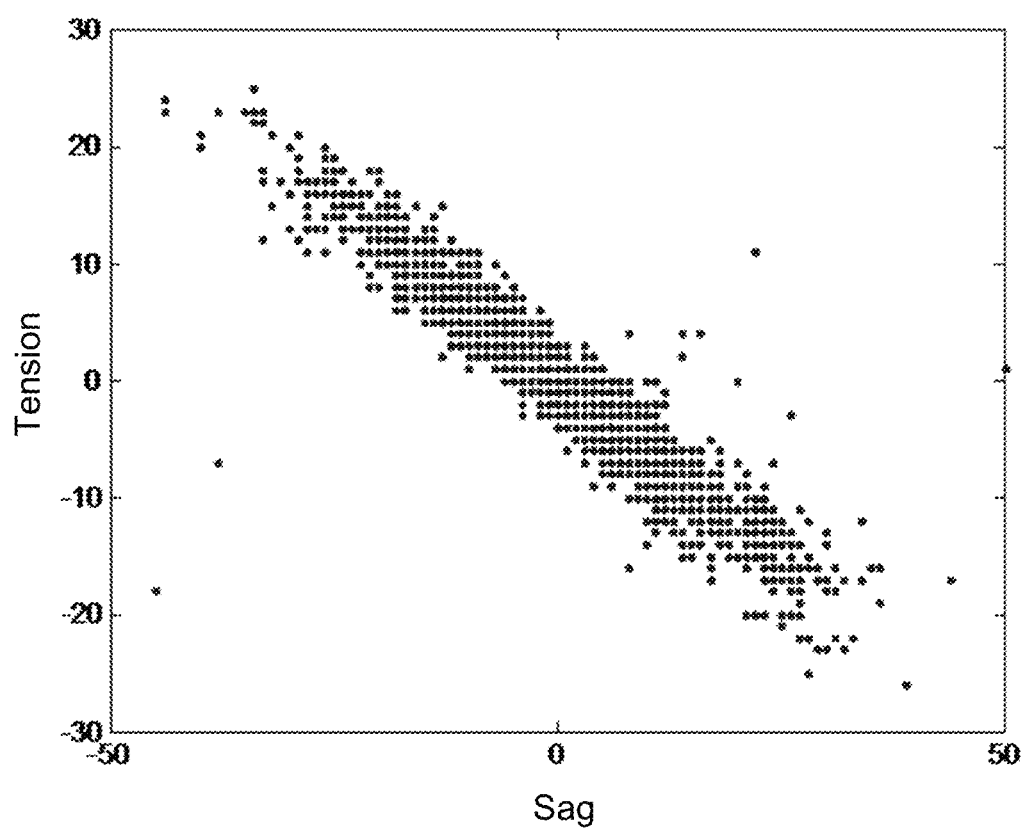
FIG. 6 is a graph showing the correlation from raw output obtained from tension sensors and sag obtained from vibration-based method.

However, it is intended to use the fact that vibration-based sag measurement determines sag (or fundamental frequency) without the need of any data. Such properties may also be used to determine many other features. As vibration-based sag measurement is obtained without the need of any data, raw tension sensor output can be fit, using equation (1), to sag in case of period of no accretion, for example during summer, with high ambient temperature, etc., with no need of calibration of the sensor before installation (raw tension and acceleration data respectively shown in FIG. 5). Such a good correlation is shown in FIG. 6, which corresponds to data collected during about one month (from 2014 May 22 to 2014 Jun. 18).

As wet snow accretes on a conductor, it tends to twist it and so to expose a fresh conductor surface for further accretion. Thus conductors that have low torsional rigidity can have higher ice loads.

Figure 7:
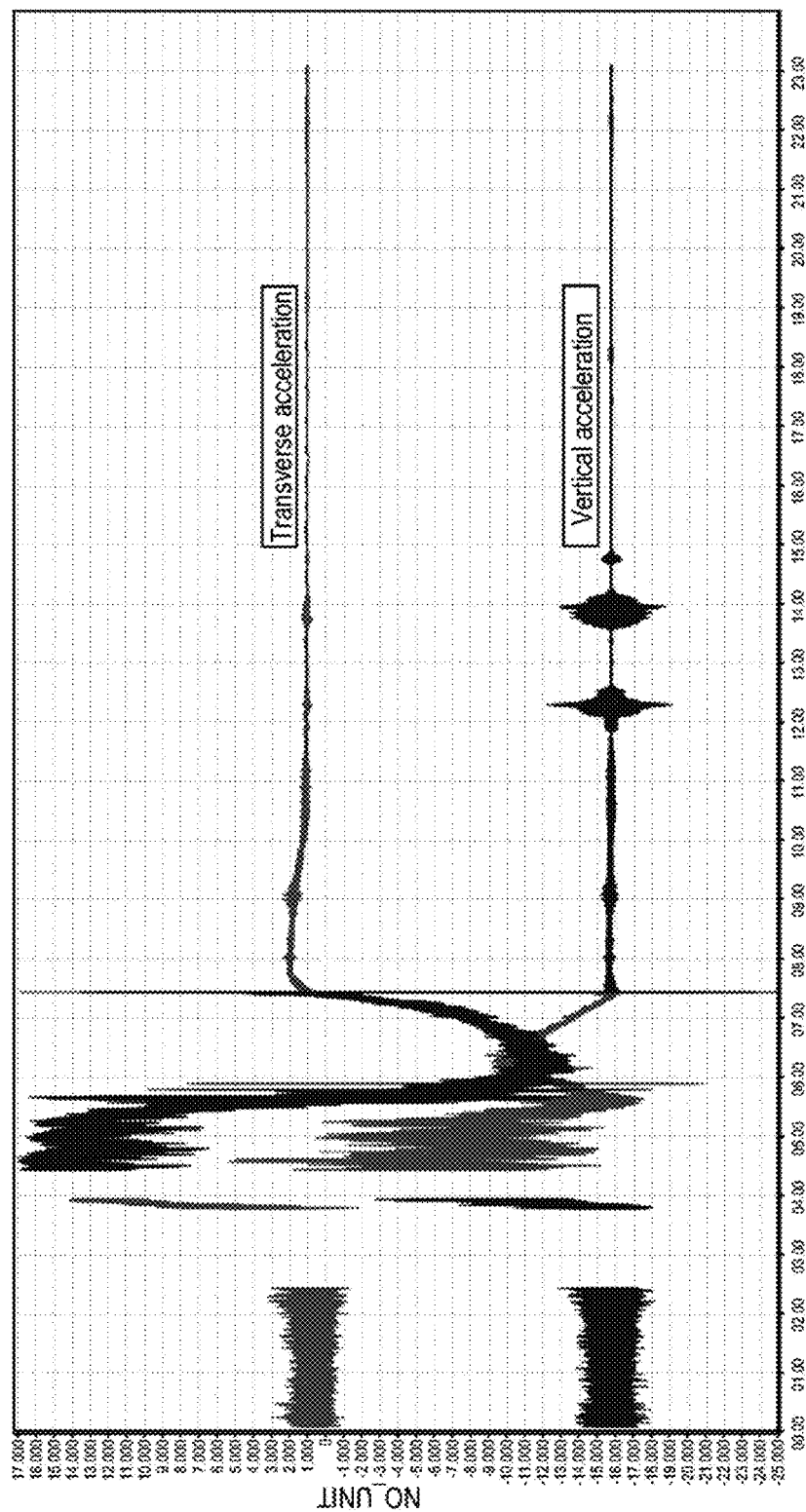
FIG. 7 is a graph illustrating the potential twist of the conductor by measuring (three-axis) acceleration of the conductor. Initial vertical axis acceleration goes from the opposite of the gravity to the gravity and comes back to the previous initial state.

In long single conductor spans, the eccentric weight of the deposit may be large enough to significantly twist the conductor. Since the conductor span is fixed against rotation at the ends, this eccentric ice load will twist the conductor most at mid-span and the angle of twist will become progressively smaller going from mid-span towards the supports. Bundled conductors have higher rotational stiffness than single conductors which leads to differences in ice accumulation and shedding. Anti-torsion devices like counterweights, detuning pendulum or spacers can reduce the amount (and shape) of snow deposit and even accelerate the snow shedding. As a consequence the observed twist, as illustrated on FIG. 7, depends on the span's configuration (single conductor, bundled conductors, interphase spacers, detuning pendulums, etc.) and depends on measurement sensor location along the span.

As vibration-based sensor as detailed in U.S. Pat. No. 8,184,015 B2 measures three-axis (static and dynamic) vibrations of conductor, this twist can be measured/observed. This is an additional information that can be advantageously used in the determination of potential ice accretion (see FIG. 7).

The method according to the invention has several advantages over the methods proposed in the art since sag and icing is simultaneous monitored without need of any, otherwise unavailable and/or uncertain, data or uncertain models.

REFERENCE SYMBOLS 1. overhead power line cable (without deflection)
2. span
3. pylon
4. autonomous sensing device
5. processing unit
6. temperature measurement
7. electric current measurement
8. internal tension sensor device
9. mechanical tension measurement
10. cavity
11. strain gauge
12. plug for power supply and tension data recovery
13. external housing
14. internal housing
15. insulation
16. energy storage means (battery, capacitors)
17. cable portion deflected by internal sensor device

REFERENCES

[1] Min Zhang, Yimeng Xing, Zhiguo Zhang and Qiguan Chen, Design and Experiment of FBG-Based Icing Monitoring on Overhead Transmission Lines with an Improvement Trial for Windy Weather, Sensors 2014, 14, 23954-23969; doi:10.3390/s141223954
[2] F. Kiessling et al, Overhead Power Lines, Planning, Design, Construction, Springer, 2003.
[3] Moser, M. J., George, B. Zangl, H. Brasseur, G., Icing detector for overhead power transmission lines, Instrumentation and Measurement Technology Conference, 2009. I2MTC '09. IEEE, pp 1105-1109.
[4] http://www.combitech.se/
[5] http://www.powerlimit.be/
http://www.powerlimit.be/files/upload/HF32.pdf
[6] https://www.tensitron.com/
https://www.tensitron.com/product/acx-1
[7] http://www.briceaust.com.au/DillonQCTM
[8] http://www.cooperinstruments.com/best-sellers/wire-tension-meters/
[9] http://russianpatents.com/patent/220/2209513.html

The invention claimed is:

1. A device for detecting and/or measuring atmospheric accretion on a suspended electrical cable span of overhead power lines, comprising:
a casing to be traversed by a portion of the cable;
a three-axis accelerometer for acquiring cable motion data over time to measure a fundamental frequency of electrical cable oscillations, said fundamental frequency being solely necessary to determine a sag of said suspended electrical cable portion, which is called the method of operations fundamental frequency;
a local mechanical tension sensor device having at least one strain gauge sensor, said local mechanical tension sensor device being arranged to impose a deflection to the cable portion traversing the casing, to obtain a deflected cable portion, and to provide a raw local tension over time as resulting output strain gauge measurements; and
a transmitter for transmitting said cable motion and raw local tension data to a data processing unit capable of detecting and/or measuring said atmospheric accretion from complementing and/or combining said sag and said raw local tension data;
wherein the local mechanical tension sensor is internal to the casing and adjusted therein to obtain a predetermined deflection, and made of a transverse mechanical compact part or support hosting a central circular cavity for accommodating the electric cable portion and applying a deflection thereto which is perpendicular to the cable axis; and
a strain gauge sensor symmetrically on each transverse side of said cavity for measuring the tension caused by the deflection.

2. The device of claim 1, further comprising a means for measuring vibrations of the cable portion in order to determine wind pressure.

3. The device of claim 2, wherein said means for measuring vibrations is the three-axis accelerometer.

4. A method for detecting and/or measuring atmospheric accretion on a suspended electrical cable span of overhead power lines, said suspended electrical cable span having a sag and a local tension, and being subject to wind pressure, by using the device of claim 3 for acquiring sag, raw local tension, and wind pressure data, independently comprising:
a first step of measuring said sag and measuring said wind pressure over a first given time range; and
a second step of measuring said raw local tension over a second given time range; the results of said first and second steps being complemented and/or combined to effect atmospheric accretion detection and/or measurement.

5. The method according to claim 4, wherein atmospheric accretion comprises ice, snow, wet snow, frost and mixtures thereof.

6. The method according to claim 4, wherein the first given time range and the second given time range are the same, with sag and icing being simultaneously monitored.

7. The method according to claim 4, wherein the step of measuring the sag of the suspended electrical cable span is solely obtained by determination of a fundamental frequency of electrical cable oscillations.

8. The method according to claim 7, wherein raw tension output data are fitted over the given time range to sag data determined by a method of oscillations fundamental frequency, said time range corresponding to a period with no atmospheric accretion and negligible wind, so that no further calibration is needed for converting raw tension output to actual tension.

9. The method according to claim 4, wherein the step of measuring the sag of the suspended electrical cable span is obtained by an optical method in which a distance to an external target or the ground is measured by a camera located in a device mounted on the suspended span.

10. The method according to claim 4, wherein the step of measuring the sag of the suspended electrical cable span is obtained using an inclinometer to measure an angle of the suspended electrical cable span with respect to the ground.

11. The method according to claim 4, wherein accretion loading by unit length $w_{ice}$ [N/m] is given by $$DH = \frac{w_c L^2}{8} \sqrt{\left(1 + \frac{w_{ice}}{w_c}\right)^2 + \left(\frac{w_{wind}}{w_c}\right)^2},$$

where D [m] is the sag, H [N] is local mechanical tension and L[m] is a length of the span, $w_c$ [N/m] is conductor weight per unit length and $w_{wind}$ [N/m] is the wind pressure per unit length.

12. The method according to claim 11, wherein, in case of negligible wind pressure, the accretion loading by unit length $w_{ice}$ [N/m] is given by $$DH = \frac{w_c L^2}{8}\left(1 + \frac{w_{ice}}{w_c}\right).$$

13. The method according to claim 4, wherein the change of accretion load, and further the change of apparent weight of span due to accretion, over time, is given by:

$$\frac{d}{dt}(DH) = \frac{L^2}{8}\frac{dw_{ice}}{dt}.$$

where D [m] is the sag, H [N] is local mechanical tension, L[m] is a length of the span, and $w_{ice}$ [N/m] is accretion loading by unit length.

14. The device of claim 1, wherein the local mechanical tension sensor comprises a plug for connecting wires for a power supply of the local mechanical tension sensor and for recovering tension data.

15. The device of claim 1, further comprising a camera for measuring the sag of the suspended electrical cable span by an optical method, in which a distance to an external target or the ground is measured by the camera mounted on the suspended electrical cable span.

16. The device of claim 1, further comprising an inclinometer for determining the sag of the suspended electrical cable span by measuring an angle of the suspended electrical cable span with respect to the ground.

17. The device of claim 1, further comprising a data processing unit capable of detecting and/or measuring said atmospheric accretion by complementing and/or combining said sag and said raw local tension data.

* * * * *